United States Patent [19]

Grimland et al.

[11] Patent Number: 4,575,042
[45] Date of Patent: Mar. 11, 1986

[54] PNEUMATICALLY AMPLIFIED CONSERVATION VALVE

[75] Inventors: Charles J. Grimland, Garland; Richard P. Cheatham, Royse City, both of Tex.

[73] Assignee: Associates of Dallas, Dallas, Tex.

[21] Appl. No.: 642,062

[22] Filed: Aug. 17, 1984

[51] Int. Cl.$^4$ .............................................. F16K 31/385
[52] U.S. Cl. .................................... 251/46; 251/28; 251/33; 251/43; 128/204.26; 128/205.24; 137/908; 137/489; 137/494
[58] Field of Search .............. 137/489.5, DIG. 9, 489; 128/204.26, 205.24; 251/28, 33, 46, 34

[56] References Cited

U.S. PATENT DOCUMENTS

| | | | |
|---|---|---|---|
| 2,480,712 | 8/1949 | Carbon | 137/139 |
| 3,300,176 | 1/1967 | Hatch, Jr. | 251/33 |
| 3,456,669 | 7/1969 | Lloyd | 137/84 |
| 3,537,448 | 11/1970 | Liston | 128/205.24 X |
| 4,054,133 | 10/1977 | Myers | 128/204.26 |
| 4,278,110 | 7/1981 | Price et al. | 137/805 |
| 4,457,340 | 7/1984 | Krueger | 137/625.5 |

FOREIGN PATENT DOCUMENTS

| | | | |
|---|---|---|---|
| 1569875 | 6/1980 | United Kingdom | 128/204.26 |
| 649430 | 4/1979 | U.S.S.R. | 128/204.26 |

*Primary Examiner*—Samuel Scott
*Assistant Examiner*—Allen J. Flanigan
*Attorney, Agent, or Firm*—Richards, Harris, Medlock & Andrews

[57] ABSTRACT

A pneumatically amplified conservation valve controls a flow of gas, such as oxygen, to a hospital patient. A sense tube monitors pressure variations as a result of exhalation by the user. The exhalation pressure variation deflects a diaphragm which closes a check valve that serves to vent gas through a bleed port. When the check valve closes the bleed gas is restricted in a chamber which deflects the diaphragm which in turn drives a connector that pushes a plunger to close a port that is connected to the source of gas through a supply tube. The gas is normally supplied through the supply tube and a normally open pneumatic valve to an output tube and then to the user. The pneumatically amplified conservation valve provides gas to the user except when the user is exhaling thereby substantially saving the amount of gas that must be provided to a user.

2 Claims, 2 Drawing Figures

4,575,042

PNEUMATICALLY AMPLIFIED CONSERVATION VALVE

TECHNICAL FIELD

The present invention pertains in general to pneumatic valves and in particular to such a valve having pneumatic amplification.

BACKGROUND ART

It has been the typical practice to dispense oxygen to a patient in a continuous flow to a mask or a cannula. However, only the oxygen delivered during the patient's inhalation cycle is actually used by the patient. The oxygen delivered during the exhalation cycle of breathing is wasted. This can result in a loss of more than half of the oxygen which is provided to a patient. As a result of this waste there is considerable additional expense in the providing of such an oxygen supply.

Various control devices have been suggested for regulating control of the supply of oxygen provided to a patient to reduce this waste. Such a control device is shown in U.S. Pat. No. 4,278,110. Such devices have not proven fully satisfactory. Problems of such devices include a slow response time which can adversely affect the patient's breathing pattern and excessive bleed flow rates which can waste a substantial quantity of oxygen.

Additional applications are available for such an oxygen regulating valve provided the valve can be used outside the carefully controlled environment of a hospital. Such other applications include fire fighters, scuba divers, pilots and athletes. Prior art devices, such as shown in U.S. Pat. No. 4,278,110 cannot be used in adverse environments due to orientation limitations.

In view of the above problems and the need for conserving oxygen supplies, there exists a requirement for an oxygen conservation valve which can rapidly respond to demand, reduce waste of oxygen to a minimum and function in environments outside of a hospital.

SUMMARY OF THE INVENTION

A selected embodiment of the present invention comprises a pneumatically amplified conservation valve for controlling gas flow from a supply tube to a user through an output tube in response to gas pressure variations received through a sense tube. The valve includes a normally open pneumatically controlled valve which is closed in response to a pressure increase in a first chamber. The pneumatically controlled valve has the input thereof connected to the supply tube and the output thereof connected to the output tube. A passage provides fluid communication between the supply tube and the first chamber. A pneumatically controlled check valve permits fluid flow from the supply tube to a bleed port. The check valve is closed in response to a pressure increase in a second chamber which is connected to the sense tube. A pressure increase received through the sense tube closes the check valve such that gas received through the passage pressurizes the first chamber to close the pneumatically controlled valve to stop the supply of said gas through said output tube.

BRIEF DESCRIPTION OF THE DRAWINGS

For a more complete understanding of the present invention and the advantages thereof, reference is now made to the following description taken in conjunction with the accompanying drawings in which.

DETAILED DESCRIPTION

Figure 1:
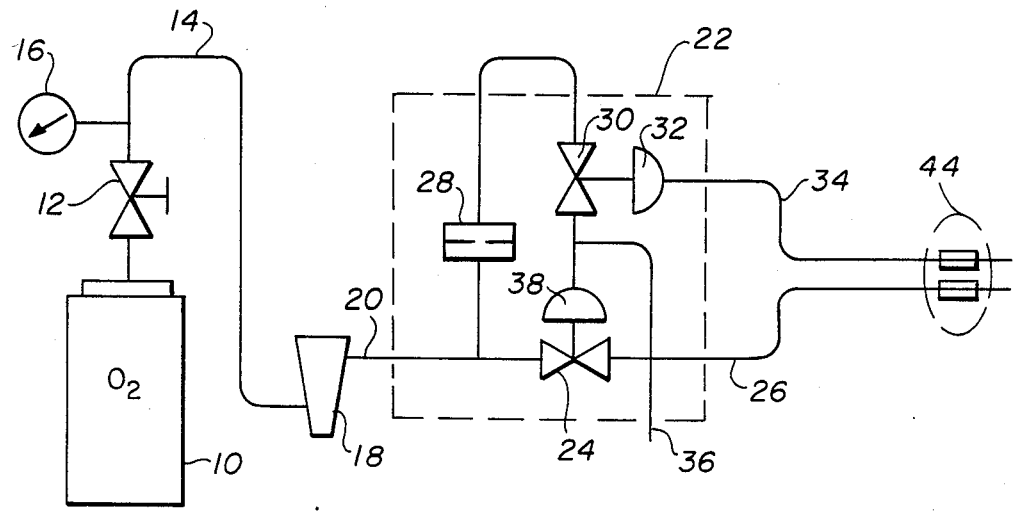
FIG. 1 is a schematic illustration of a complete system of oxygen supply which includes a pneumatically amplified conservation valve in accordance with the present invention.

Referring now to FIG. 1 there is illustrated an overall system for using the pneumatically amplified conservation valve of the present invention. An oxygen supply tank 10 is connected through a valve 12 to a line 14. A gauge 16 is connected to monitor the pressure in line 14. A flow meter 18 is connected in line 14 to measure the flow of oxygen through line 14. The output of the flow meter 18 is connected to a supply tube 20 which is connected to a pneumatically amplified conservation valve 22 in accordance with the present invention. The valve 22 is illustrated schematically in FIG. 1 and is illustrated as a detailed mechanical drawing in FIG. 2.

Schematically, the valve 22 comprises a pneumatically controlled normally open valve 24 which is connected between the supply tube 20 and an output tube 26. A flow restrictor 28 is connected between the supply tube 20 and the input of a pneumatically controlled valve 30. The valve 30 is controlled by a pneumatic diaphragm 32 which is in turn connected to a sense tube 34. The output of valve 30 is further connected to a bleed port 36. The output of valve 30 is connected to a pneumatic diaphragm 38 which in turn controls the valve 24.

The tubes 26 and 34 are connected to a cannula 44 which is typically inserted into a patient's nostrils.

Further referring to FIG. 1, the valve 24 is normally open thereby providing a flow of oxygen from tube 20 through valve 24 and through tube 26 to the cannula 44. When the patient exhales a slight increase in pressure is created in the tube 34 which activates the diaphragm 32 for closing the valve 30. This in turn activates the diaphragm 38 to close the normally open valve 24. As a result, the flow of oxygen through valve 22, tube 26 is stopped for so long as the patient is exhaling. As soon as the patient stops exhaling, the valve 24 is opened thereby resuming the flow of oxygen to the cannula 44.

Figure 2:
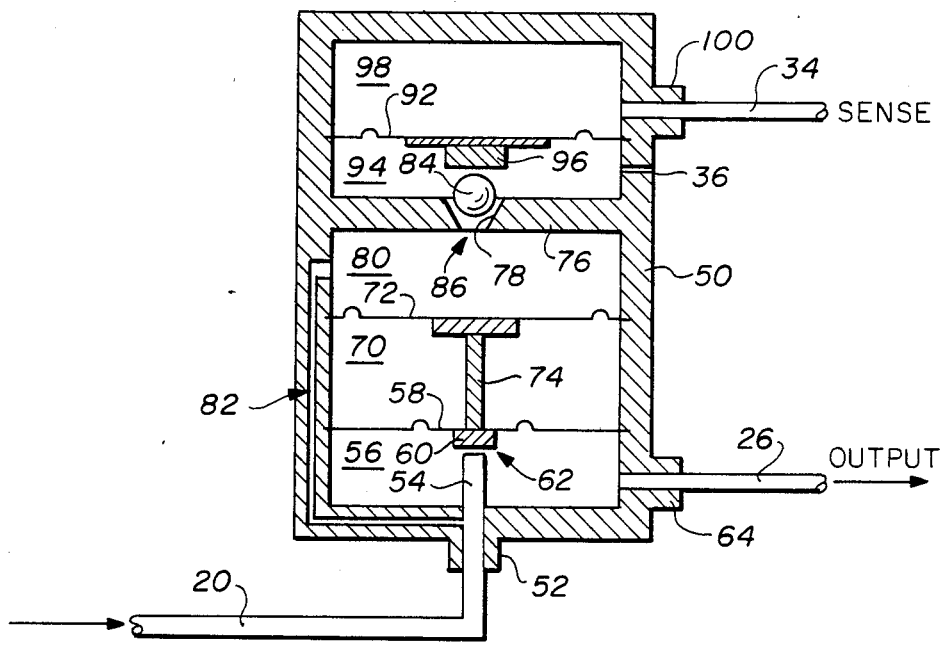
FIG. 2 is a sectional elevation view of a preferred embodiment of the pneumatically amplified conservation valve of the present invention.

Referring now to FIG. 2 there is illustrated a sectional view of the pneumatically amplified conservation valve 22 shown in FIG. 1. The valve 22 includes a housing 50. The supply tube 20 is connected through a tubing connector 52 through the housing 50 to a tubular shaped port 54. The port 54 is within an inlet chamber 56 which is defined by the housing 50 and a diaphragm 58.

A plunger 60 is mounted on the bottom of the diaphargm 58 such that the plunger 60 can be depressed to close the port 54. The combination of the plunger 60 and the port 54 comprises a normally open valve 62. The output tube 26 is connected through a tubing connector 64 such that the output tube 26 is in fluid communication with the chamber 56.

Above the chamber 56 there is provided a chamber 70 which is between the diaphragm 58 and a diaphragm 72. A connector 74 is connected to the diaphragm 72 and extends downward to touch the upper surface of the diaphragm 58. The active area of diaphragm 72 is substantially greater than the active area of the diaphragm 58. This difference provides pneumatic amplification.

The housing 50 includes an interior divider wall 76 which has a conical orifice 78. A chamber 80 is between the diaphragm 72 and the wall 76.

A restricting passage 82 provides fluid flow between the supply tube 20 and the chamber 80.

A ball 84 is provided to seat in the orifice 78 such that the combination of the ball 84 and the orifice 78 forms a check valve 86. A diaphragm 92 defines a chamber 94 between the diaphragm 92 and the wall 76. A piston 96 is connected to the bottom of the diaphragm 92 such that when the diaphragm 92 is depressed the piston 96 forces the ball 84 into the orifice 78 thereby closing the valve 86.

A chamber 98 is defined by the housing 50 and the diaphragm 92. The sense tube 34 is connected through a tubing coupler 100 to provide fluid communication between the tube 34 and the chamber 98.

The bleed port 36 passes through the housing 50 into the chamber 94.

Operation of the valve 22 is now described in reference to FIG. 2. Oxygen is supplied to the supply tube 20 into the chamber 56 at a regulated pressure. When the valve 62 is open, that is, the plunger 60 is not closing the port 54, oxygen flows through chamber 56 to the output tube 26 and from there to the patient.

A supply of the pressure regulated oxygen is also transmitted through the restricted passage 82 into the chamber 80. The oxygen which flows through this line is termed the bleed gas. This bleed gas causes the ball 84 to be lifted such that the gas enters the chamber 94 and exits the housing 50 through the port 36. Thus, the patient is supplied with oxygen when he is not exhaling. When the patient exhales there is created a small increase in pressure in the sense tube 34. This increase in pressure is transmitted to the chamber 98. This pressure increase causes the diaphragm 92 to be depressed thereby forcing the ball 84 into the orifice 78. This blocks the flow of the bleed air from the chamber 80. The increase in pressure in the chamber 80 forces the diaphragm 72 downward. The connector 74 is also forced downward to drive the diaphragm 58 and plunger 60 downward to seal the port 54. This stops the flow of oxygen into the chamber 56 and therefore stops the flow of oxygen through the output 26 to the patient. The port 54 is blocked only for the time that the patient is exhaling. When the patient ceases exhaling the pressure in chamber 98 is relieved and the diaphragm 92 is permitted to return to its normal position. This permits the ball 84 to rise and allow the bleed gas from chamber 80 to pass out through the port 36. The diaphragm 72 and connector 74 rise thereby removing the plunger 60 from the port 54 to restore the flow of oxygen through the chamber 56 and through the output tube 26 to the patient.

The large area of the diaphragm 72 as compared to the diaphragm 58 provides pneumatic amplification. The large area of the diaphragm 92 further provides pneumatic amplification for operating the ball 84 on the check valve 86. The combination of the check valve 86 and the diaphragm 92 provides pneumatic gain on the order of several thousand.

In a selected embodiment of the present invention, the operating gas is oxygen, oxygen enriched air or plain air. The gas throughput is in a range of zero to 20 liters per minute depending upon the supply pressure and the patient breathing pattern. The gas supply pressure is typically between 3 and 50 pounds per square inch. The response time to the patient exhalation to terminate or start the flow of oxygen is approximately 0.25 seconds maximum. The valve 22 is responsive to a sense pressure in tube 34 of no more than 0.002 pounds per square inch. This in turn can control a flow from a source of 50 pounds per square inch, yielding a pneumatic gain of over 25,000. The flow rate of gas through the bleed port is approximately 0.2 liters per minute during inhalation and zero during exhalation. The valve 22 can be oriented in 2 degrees of freedom since it has only one ball valve. A preferred size for the housing 50 is a cylinder 2⅝ inches in diameter and 2⅜ inches long. A selected weight is 4 ounces. In a typical application the valve 22 is positioned on a table top or suspended by a hook.

Although one embodiment of the invention has been illustrated in the accompanying drawings as described in the foregoing Detailed Description, it will be understood that the invention is not limited to the embodiment disclosed, but is capable of numerous rearrangements, modifications and substitutions of parts and elements without departing from the scope of the invention.

What we claim is:

1. A pneumatically amplified conservation valve for controlling gas flow from a supply tube to a user through an output tube in response to gas pressure variations received through a sense tube, the valve comprising:
   a normally open pneumatically controlled valve which is closed in response to a pressure increase in a first chamber, said pneumatically controlled valve having the input thereof connected to said supply tube and the output thereof connected to said output tube,
   a passage for providing fluid communication between said supply tube and said first chamber,
   a pneumatically controlled check valve to permit fluid flow from said first chamber to a bleed port, said check valve closed in response to a pressure increase in a second chamber which is connected to said sense tube, whereby a pressure increase received through said sense tube closes said check valve such that gas received through said passage pressurizes said first chamber to close said pneumatically controlled valve to stop the supply of said gas to said output tube,
   said pneumatically controlled check valve including a ball,
   a plate which serves as a wall of said first chamber, said plate having a conical orifice therethrough for receiving said ball for permitting the flow of said gas only out of said first chamber,
   a diaphragm closing said second chamber, said diaphragm deflected by gas pressure received through said sense tube, and
   a piston connected to said diaphragm facing said ball for forcing said ball to close said conical orifice when said diaphragm is deflected toward said ball.

2. A pneumatically amplified conservation valve for controlling gas flow from a supply line to a user through an output line in response to gas pressure variations received through a sense tube, the valve comprising:
   a housing having an interior wall which divides the interior volume of the housing into first and second compartments, a first diaphragm connected to the interior surface of said housing in said first compartment to form a first compartment, a tubular port extending through a wall of said housing into said first chamber, said output tube connected through the wall of said housing for fluid communication with said first chamber, a plunger connected to said first diaphragm facing said tubular port for closing said port when said diaphragm is deflected toward said port, a second diaphragm connected to the interior surfaces of said housing in said first compartment to form with said interior wall a second chamber, said second diaphragm having a greater area than said first diaphragm, a restricted passageway extending from said tubular port to said second chamber, said passageway for providing bleed gas to said second chamber, a connector extending from said second diaphragm to touch said first diaphragm opposite said plunger, said interior wall having a conical orifice therein with the smaller end of said orifice opening to said second chamber, a ball for receipt into said orifice wherein said ball and said orifice function as a check valve to permit gas flow only from said second chamber through said orifice, a third diaphragm dividing said second compartment into third and fourth chambers, said third chamber between said interior wall and said third diaphragm, said fourth chamber in fluid communication with said sense tube, a bleed port extending from said third chamber to outside said housing, and a piston connected to said third diaphragm and facing said ball for driving said ball to close said orifice when said fourth chamber receives gas pressure from said sense tube.

* * * * *